US009683217B2

(12) United States Patent
Ince et al.

(10) Patent No.: US 9,683,217 B2
(45) Date of Patent: Jun. 20, 2017

(54) IN VITRO CULTURE CONDITIONS FOR T-CELL ACUTE LYMPHOBLASTIC LEUKEMIA/LYMPHOMA

(71) Applicants: THE UNIVERSITY OF MIAMI, Miami, FL (US); The Brigham and Women's Hospital, Inc., Boston, MA (US)

(72) Inventors: Tan A. Ince, Miami, FL (US); Jon C. Aster, Lexington, MA (US)

(73) Assignees: UNIVERSITY OF MIAMI, Miami, FL (US); The Brigham and Women's Hospital, Inc., Boston, MA (US)

( * ) Notice: Subject to any disclaimer, the term of this patent is extended or adjusted under 35 U.S.C. 154(b) by 0 days.

(21) Appl. No.: 14/394,346

(22) PCT Filed: Apr. 12, 2013

(86) PCT No.: PCT/US2013/036357
§ 371 (c)(1),
(2) Date: Oct. 14, 2014

(87) PCT Pub. No.: WO2013/155405
PCT Pub. Date: Oct. 17, 2013

(65) Prior Publication Data
US 2015/0119557 A1    Apr. 30, 2015

(51) Int. Cl.
*C12N 5/09*    (2010.01)
*G01N 33/50*   (2006.01)
*C07K 16/28*   (2006.01)

(52) U.S. Cl.
CPC ............ *C12N 5/0694* (2013.01); *C07K 16/28* (2013.01); *C07K 16/2863* (2013.01); *G01N 33/505* (2013.01); *G01N 33/5011* (2013.01); *C07K 2317/73* (2013.01); *C07K 2317/76* (2013.01); *C12N 2500/92* (2013.01); *C12N 2501/105* (2013.01); *C12N 2501/11* (2013.01); *C12N 2501/125* (2013.01); *C12N 2501/2302* (2013.01); *C12N 2501/2307* (2013.01); *C12N 2501/26* (2013.01); *C12N 2501/33* (2013.01); *C12N 2501/39* (2013.01); *C12N 2501/395* (2013.01); *C12N 2501/42* (2013.01); *C12N 2502/1394* (2013.01); *G01N 2500/10* (2013.01)

(58) Field of Classification Search
CPC ........ C12N 2501/105; C12N 2501/125; C12N 2501/2302; C12N 2501/2307; C12N 5/0694
See application file for complete search history.

(56) References Cited

U.S. PATENT DOCUMENTS

| | | |
|---|---|---|
| 8,252,591 B2 | 8/2012 | Ince |
| 2008/0299540 A1 | 12/2008 | Ince |
| 2011/0244502 A1 | 10/2011 | Ince |
| 2013/0055417 A1 | 2/2013 | Ince |
| 2014/0170693 A1 | 6/2014 | Ince |

OTHER PUBLICATIONS

Ince et al., Cancer Cell 12:160-170, 2007.*
Int'l Search Report for PCT/US2013/036357, two pages (Aug. 2013).
Written Opinion for PCT/US2013/036357, three pages (Aug. 2013).
Armstrong et al. "NOTCH is a key regulator of human T-cell acute leukemia initiating cell activity" *Blood*, vol. 113, No. 8, pp. 1730-1740 (Feb. 2009).
Bruserud et al. "In vitro culture of human acute lymphoblastic leukemia (ALL) cells in serum-free media; a comparison on native ALL blasts, ALL cell lines and virus-transformed B cell lines" *Leukemia Research*, vol. 27, No. 5, pp. 455-464 (2003).
Joshi et al. "Preferential in-vitro growth and expansion of leukemic T lymphoblasts" *Leukemia Research*, vol. 12, No. 2, pp. 103-108 (1988).
Yost et al. "Defined, serum-free conditions for in vitro culture of primary human T-ALL blasts" *Leukemia*, vol. 27, No. 6, pp. 1437-1440 (Jun. 2013).

* cited by examiner

*Primary Examiner* — Daniel C Gamett
(74) *Attorney, Agent, or Firm* — Marshall, Gerstein & Borun LLP

(57) ABSTRACT

We describe cell culture media for in vitro culture of a human cancer cell of the lymphocyte lineage (e.g., leukemia, lymphoma, or other blasts) or a precursor thereof, especially T-cell acute lymphoblastic leukemia lymphoma (T-ALL), as well as methods for at least maintenance, propagation, or both of the human cancer cell or its precursor.

37 Claims, 6 Drawing Sheets

IN VITRO CULTURE CONDITIONS FOR T-CELL ACUTE LYMPHOBLASTIC LEUKEMIA/LYMPHOMA

CROSS-REFERENCE TO RELATED APPLICATION

This application is the U.S. national phase of International Application No. PCT/US2013/036,357, filed 12 Apr. 2013, which designated the U.S. and claims priority benefit of provisional U.S. Application No. 61/623,539, filed Apr. 12, 2012; the entire contents of each of which are hereby incorporated by reference.

BACKGROUND

Improvements are provided for in vitro culturing of a human cancer cell of the lymphocyte lineage (e.g., leukemia or lymphoma), another lymphoblast, or a precursor thereof, especially T-cell acute lymphoblastic leukemialymphoma (T-ALL).

T-ALL is an aggressive malignancy for which optimization of chemotherapy has led to steady improvements in outcome for pediatric patients. But 20-25% of pediatric patients fail current chemotherapy regimens, and outcomes in adult patients are not as good as for children. For this group of patients, new effective therapies are desperately needed. In addition, current effective therapies in children require up to two years of treatment with highly toxic drug combinations. Therefore, there is a need for more effective and less toxic treatments in this disease.

Efficient testing and validation of novel therapies would be greatly enhanced by development of a robust in vitro culture model that allows direct assay of primary human T-ALL blasts. Most efforts to date have relied heavily upon established cell lines, which are adapted to growth in high concentrations of serum and have certain molecular features (e.g., high frequency of p53 mutations) that are not present in primary tumors. While primary patient T-ALL samples can be expanded as xenografts in immunodeficient mice (see Armstrong et al., Blood 113:1730-1740, 2009; Chiu et al., Blood 116:5268-5279, 2010; Cox et al., Blood 109:674-682, 2007; Medyouf et al., Blood 115:1175-1184, 2010), such in vivo studies are costly and time consuming. They are often complicated by the poor health of immunodeficient mice, precluding optimal drug dosing.

Several groups have reported cell culture of primary human T-ALL in vitro with supplemental cytokines, although results were typically highly variable and, in many cases, cultures have likely undergone crisis prior to the expansion phase, suggesting the outgrowth of a minor subpopulation or variant subclone. A co-culture system for human T-ALL uses a feeder layer (i.e., mouse stromal cells) that express Notch ligand Delta-like-1 (DL1) to activate Notch signaling and further sustain blast cell growth (Armstrong et al., Blood 113:1730-1740, 2009; Chiu et al., Blood 116: 5268-5279, 2010). For example, Pflumio medium containing a mixture of fetal calf serum and human serum was used to culture human T-ALL in vitro over an MS5-DL1 feeder layer. But there is substantial variability in different serum lots for their ability to support cell maintenance and propagation.

Thus, an in vitro culturing system for primary T-ALL to study specific gene mutation, chromosome rearrangement, epigenetic changes in DNA methylation or chromatin, drug resistance, expression of cell markers and their function, immunogenicity, progression through the cell cycle and apoptosis, sensitivity to a therapeutic agent, or any combination thereof would be desirable. In vitro culturing may be used to identify a precursor cell that gives rise to T-ALL (i.e., cancer stem cell), to differentiate T-ALL, or to determine whether T-ALL disease is clonal. For heterogeneous cells, a T-ALL subpopulation may be subcloned by cell separation or dilution.

Here, a serum-free, chemically-defined medium previously used for in vitro culture of mammary epithelium (Ince et al., Cancer Cell 12:160-170, 2007) is modified by excluding cholera toxin and including additional components to support the growth of T-ALL. US20080299540 described a similar cell culture medium, different from the medium disclosed herein, without mentioning supporting the maintenance and propagation of T-ALL.

It is an objective to provide an in vitro culture system for improved maintenance and propagation of human cancer cells of the lymphocyte lineage (e.g., leukemia or lymphoma), other lymphoblasts, or precursors thereof, especially T-cell acute lymphoblastic leukemialymphoma (T-ALL). The system may be used to expand or to examine the cell. A chemically-defined, cell culture medium and a method for in vitro culturing of one or more human cell(s) are provided as improvements over the prior art.

SUMMARY

A first objective is to provide an in vitro cell culture medium. The medium may be comprised of at least: optionally epidermal growth factor (EGF), optionally hydrocortisone, optionally insulin, stem cell factor (SCF), insulin-like growth factor-1 (IGF-1), inter-leukin-2 (IL-2), and interleukin-7 (IL-7). The medium may be further comprised of one or more of the following: precursors of lipid synthesis, precursors of protein synthesis, precursors of carbohydrate synthesis, precursors of energy metabolism, precursors in a catabolic or anabolic metabolic pathway, antioxidants, precursors of nucleotide synthesis in a salvage pathway, carrier proteins, surfactants, salts, buffers, and any combination thereof.

Alternately, the medium may be comprised of at least: vitamin A, vitamin B1, vitamin B2, vitamin B3, vitamin B5, vitamin B6, vitamin B7, vitamin B9, vitamin B12, vitamin C, vitamin D, and vitamin E; zinc, magnesium, iron, copper, and selenium; transferrin and albumin; cholesterol, linoleic acid, and lipoic acid; triiodothyronine (T3); glucose; glutathione; adenosine triphosphate; phosphoethanolamine; one or more precursors of the nucleotide salvage pathway selected from the following: hypoxanthine, xanthine, adenine, guanine, and thymidine; optionally epidermal growth factor (EGF); optionally hydrocortisone; optionally insulin; stem cell factor (SCF); insulin-like growth factor-1 (IGF-1); interleukin-2 (IL-2); and interleukin-7 (IL-7).

A second objective is use of any of the aforementioned in vitro cell culture media at least to maintain or to propagate a human cancer cell, including leukemia or lymphoma (e.g., T-ALL), and a precursor thereof. The cell may be a primary or precursor cancer cell from a human patient, especially of a lymphocyte lineage. Such culturing may be used in a process for screening, isolating, cloning, identifying, analyzing, or any combination thereof one or more cancer cell(s). Cells may be maintained for at least ten days, at least 20 days, at least 30 days, or at least 60 days without senescence. Cells may be propagated for at least ten population doublings, at least 20 population doublings, or at least 30 population doublings without senescence.

A third objective is use of an in vitro cell culture medium comprised of at least interleukin-7 (IL-7) and a substrate at least partially covered by a ligand for Notch receptor at least to maintain or to propagate a human cancer cell, including leukemia or lymphoma (e.g., T-ALL), and precursors thereof. The cell may be a primary or precursor cancer cell from a human patient, especially of a lymphocyte lineage. Such culturing may be used in a process for isolating, cloning, identifying, analyzing, or any combination thereof one or more cancer cell(s). Cells may be maintained for at least ten days, at least 20 days, at least 30 days, or at least 60 days without senescence. Cells may be propagated for at least ten population doublings, at least 20 population doublings, or at least 30 population doublings without senescence.

A fourth objective is to provide an in vitro culturing method of one or more human cancer cell(s), including leukemia or lymphoma (e.g., T-ALL), and precursors thereof. The method comprises incubating one or more cell(s) in an in vitro culture comprised of any of the aforementioned in vitro cell culture media. The in vitro culture may be further comprised of a substrate covered by a ligand for Notch receptor. The cell may be a primary or precursor cancer cell from a human patient, especially of a lymphocyte lineage. Such culturing may be used in a process for isolating, cloning, identifying, analyzing, or any combination thereof one or more cell(s). Cells may be maintained for at least ten days, at least 20 days, at least 30 days, or at least 60 days without senescence. Cells may be propagated for at least ten population doublings, at least 20 population doublings, or at least 30 population doublings without senescence.

Any of the aforementioned in vitro cell culture media may contain EGF is at a concentration from 5 ng/ml, up to 500 ng/ml, or both (e.g., from 5 ng/ml to 500 ng/ml).

Any of the aforementioned in vitro cell culture media may contain hydrocortisone at a concentration from from 0.05 ng/ml, up to 5 ng/ml, or both (e.g., from 0.05 ng/ml to 5 ng/ml).

Any of the aforementioned in vitro cell culture media may contain insulin at a concentration from from 1 μg/ml, up to 100 μg/ml, or both (e.g., from 1 μg/ml to 100 μg/ml).

Any of the aforementioned in vitro cell culture media may contain SCF at a concentration from 5 ng/ml, up to 500 ng/ml, or both (e.g., from 5 ng/ml to 500 ng/ml).

Any of the aforementioned in vitro cell culture media may contain IGF-1 at a concentration from 1 ng/ml, up to 100 ng/ml, or both (e.g., from 1 ng/ml to 100 ng/ml).

Any of the aforementioned in vitro cell culture media may contain IL-2 at a concentration, from 1 ng/ml, up to 100 ng/ml, or both (e.g., from 1 ng/ml to 100 ng/ml).

Any of the aforementioned in vitro cell culture media may contain IL-7 at a concentration from 1 ng/ml, up to 100 ng/ml, or both (e.g., from 1 ng/ml to 100 ng/ml).

Any of the aforementioned in vitro cell culture media may exclude a variable source of growth factors and hormones, such as serum. For example, they may be essentially serum free, contain less than 0.01% (vol/vol), contain less than 0.1% (vol/vol), contain less than 1% (vol/vol), or contain less than 10% (vol/vol) of serum. Any of the aforementioned in vitro cell culture media may also exclude FMS-like tyrosine kinase 3 ligand (Flt3L), macrophage colony stimulating factor (M-CSF), or both.

Any of the aforementioned in vitro cell culture media may also exclude erythropoietin (Epo), granulocyte colony stimulating factor (G-CFS), or both.

Any of the aforementioned in vitro cell culture media may also exclude interleukin-3 (IL-3), interleukin-6 (IL-6), or both.

A fifth objective is to provide a process of screening for an agent that affects a human cancer cell, including leukemia or lymphoma (e.g., T-ALL), and a precursor thereof. The process is comprised of:
(a) adding one or more candidate agents to an in vitro culture, which is comprised of human cancer cells and the aforementioned medium;
(b) measuring an activity or property of the human cancer cells in the presence of the one or more candidate agents; and
(c) selecting at least one agent, from among the candidate agents, that affects the human cancer cells by a change in the activity or property.

A sixth objective is to provide an agent that affects T-ALL, wherein the agent may be selected by the aforementioned process.

Further aspects will be apparent to a person skilled in the art from the following description and claims, and generalizations thereto.

DESCRIPTION OF DRAWINGS

In FIG. 4A, cells were cultured in WIT-L medium on bare plastic plates or on an MS5-DL1 feeder layer. Cells were cultured and passaged as described in FIG. 1. Data shown are a composite of passages 1 and 2. In FIG. 4B, cells were cultured in WIT-L medium on either bare plastic plates or plates coated with varying concentrations of immobilized DL1 protein. In FIG. 4C, cells were cultured in MS5-DL1 conditioned WIT-L medium on either bare plastic plates or plates coated with different concentrations of immobilized DL1 protein. Cells were cultured for 11 days, then assayed for growth with a resazurin reduction assay. Significance: * p<0.05,  p<0.01, and * p<0.001.

DESCRIPTION OF SPECIFIC EMBODIMENTS

Figure 1A:
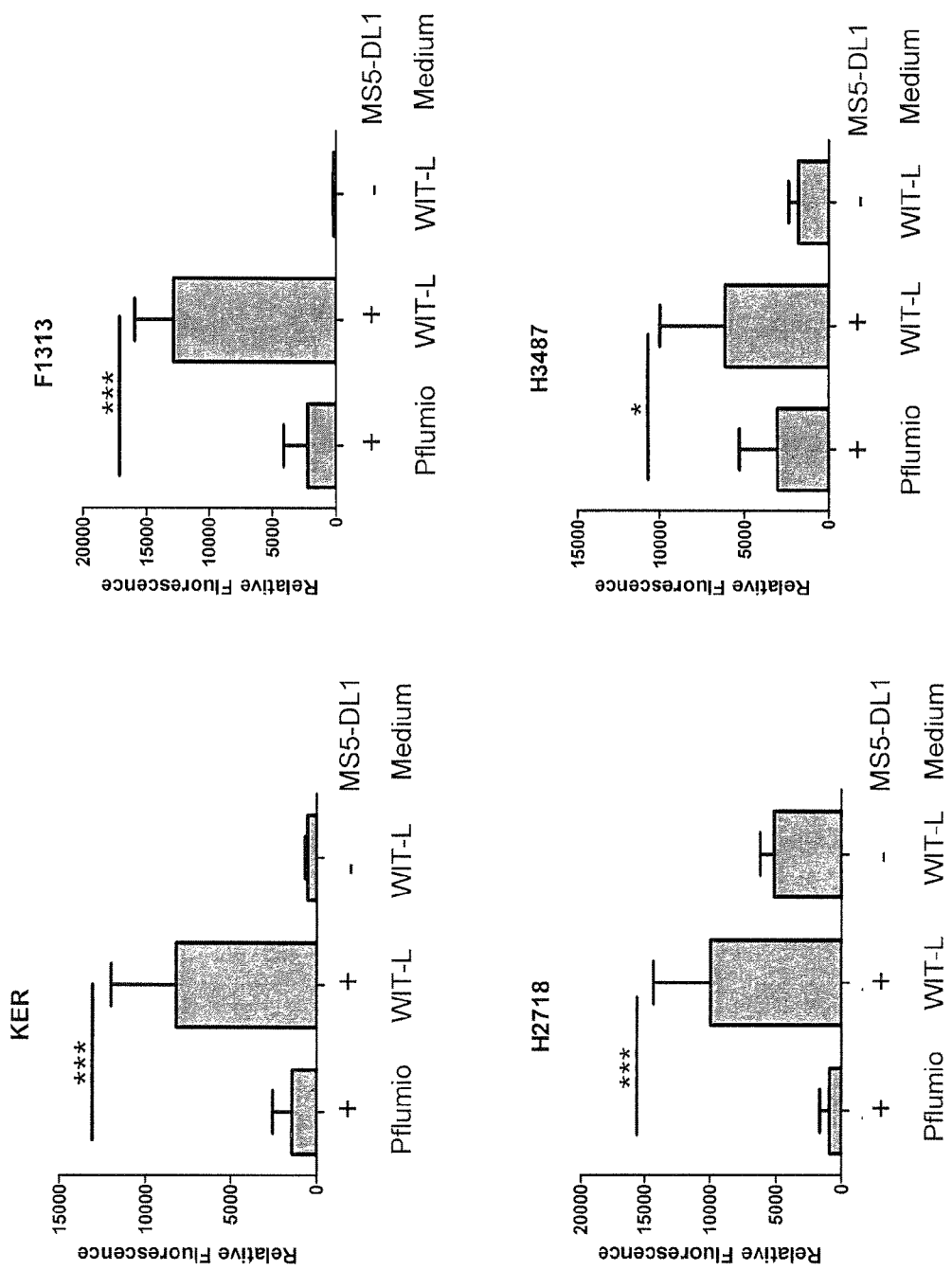
FIG. 1 shows that WIT-L medium supported improved growth of T-ALL blasts from a human patient. WIT-L serum-free media supports the improved growth of patient T-ALL blasts. A resazurin-reduction cell growth assay was performed on (A) primary (n=4) and (B) xenograft-expanded T-ALL (n=4). Cryopreserved cells were pre-cultured on an irradiated MS5-DL1 feeder layer in Pflumio medium for 2-3 days, then passaged onto another freshly irradiated MS5-DL1 feeder layer in either WIT-L or Pflumio medium. Cells were assayed for growth using a resazurin reduction assay 4-6 days later. Cells were passaged a second time under identical media conditions and growth measured again. Data shown are a composite of passages 1 and 2. Significance: * $p<0.05$,  $p<0.01$, and * $p<0.001$.

An in vitro cell culture medium may be used at least to maintain or to propagate a cancer cell, such as a leukemia or lymphoma (e.g., T-cell acute lymphoblastic leukemialymphoma or T-ALL). The medium may or may not be comprised of epidermal growth factor (EGF), hydrocortisone, insulin, stem cell factor (SCF), insulin-like growth factor-1 (IGF-1), interleukin-2 (IL-2), and interleukin-7 (IL-7). The medium may be further comprised of one or more of the following: one or more precursor(s) of lipid synthesis, one or more precursor(s) of protein synthesis, one or more precursor(s) of carbohydrate synthesis, one or more precursor(s) of energy metabolism, one or more precursor(s) in a catabolic or anabolic metabolic pathway, one or more precursor(s) of nucleotide synthesis in a salvage pathway, antioxidants, trace metals, enzyme cofactors, vitamins, carrier proteins, surfactants, salts, buffers, and any combination thereof.

Lipid synthesis precursors are one or more of the following: cholesterol, linoleic acid, lipoic acid, and o-phosphoryl ethanolamine.

Protein synthesis precursors include amino acids. For example, the amino acids that are included may be the following: glutamine, glycine, L-alanine, L-arginine, L-asparagine, L-aspartic acid, L-cysteine, L-cystine, L-glutamic acid, L-glutamine, L-histidine, L-isoleucine, L-leucine, L-lysine, L-methionine, L-phenylalanine, L-proline, L-serine, L-threonine, L-trypto-phan, L-tyrosine, and L-valine. In some other embodiments, only essential amino acids are included in the medium. Certain human cancer cells must have adequate amounts of nine amino acids to survive. These so called essential amino acids cannot be synthesized from other precursors. Cysteine can partially meet the need for methionine because they both contain sulfur. Tyrosine can partially substitute for phenylalanine. Essential amino acids include: histidine, isoleucine, leucine, lysine, methionine (and/or cysteine), phenylalanine (and/or tyrosine), threonine, tryptophan, and valine. In certain embodiments, only histidine, isoleucine, leucine, lysine, threonine, tryptophan, and valine are included in the medium. One or more polyamines (e.g., putrescine) may be included.

Energy metabolism precursors are usually carbohydrates. They may overlap with carbohydrate synthesis precursors, such as deoxy-D-ribose, D-glucose and pyruvate. But since amino acids and lipids may also be energy metabolism precursors, such composition may also overlap with lipid synthesis precursors and/or protein synthesis precursors.

Nucleotide salvage pathway synthesis precursors are one or more of the following: hypoxanthine, xanthine, adenine, guanine, and thymidine. Thymine and/or uracil may also be included.

Antioxidants are one or more of the following: glutathione, dithiothreitol (DTT), vitamin C (ascorbic acid), vitamin D (e.g., calciferols and their precursors), vitamin E (e.g., tocopherol and tocotrienol isomers), and vitamin K3 (menadione). Optionally, they may by supplemented with trace metals (e.g., Zn, Se, Cr, Cu, Mg, Mn, or a combination thereof).

Many enzymes use cofactors. If the cofactor is organic, then it is called a coenzyme. Other vitamins such as vitamin A (e.g., retinal, retinol, and other carotenoids), vitamin B1 (thiamin), vitamin B2 (riboflavin), vitamin B3 (niacin) or niacinamide, vitamin B5 (panthothenate), vitamin B6 (e.g., pyridoxal, pyridoxamine, and pyridoxine), vitamin B7 (biotin), vitamin B9 (folate) and its precursor paraamino-benzoic acid (PABA), and vitamin B12 (cobalamin) may be included. Other cofactors that may be included are choline chloride and i-inositol. Calcium (e.g., $CaCl_2$), copper (e.g., $CuSO_4$), iron (e.g., $FeNO_3$ and $FeSO_4$), KCl, NaCl, $CH_3COONa$, $NaHCO_3$, $Na_2HPO_4$, $NaH_2PO_4$, $Na_2SO_4$, selenium (e.g., $Na_2SeO_3$), zinc (e.g., $ZnSO_4$), or any combination thereof may be included. Additional inorganic salts that are optional components may be the following: magnesium (e.g., $MgCl_2$ and $MgSO_4$), manganese (e.g., $MnCl_2$), silicon (e.g., $Na_2SiO_3$), molybdenum (e.g., $(NH_4)_6Mo_7O_{24}$), vanadium (e.g., $NH_4VO_3$), nickel (e.g., $NiSO_4$), and tin (e.g., SnCl).

Albumin, ceruloplasmin, transcortin, transferrin, transthyretin, and thyroxine-binding globulin are examples of carrier proteins. A surfactant, such as TWEEN 80 or PLURONIC F68, may promote suspension culture by reducing shear force. The medium may be further comprised of at least one buffer, such as N-[2-hydroxyethyl]-piperazine-N'-[2-ethanesulfonic acid] (HEPES), $CO_2$ gas and bicarbonate, or both. A pH indicator such as phenol red may be included. Phosphate buffers are generally avoided because relatively insoluble complexes are formed with essential divalent cations at relevant concentrations.

Alternately, an in vitro cell culture medium may be comprised of vitamin A, vitamin C, and vitamin D; zinc, magnesium, iron, copper, and selenium; transferrin and albumin; cholesterol, linoleic acid, and lipoic acid; triiodothyronine (T3); glutathione; adenosine triphosphate; phosphoethanolamine; one or more precursor bases of the nucleotide salvage pathway (e.g., hypoxanthine, xanthine, adenine, guanine, and/or thymidine); epidermal growth factor (EGF); optionally hydrocortisone; insulin; stem cell factor (SCF); insulin-like growth factor-1 (IGF-1); interleukin-2 (IL-2); and inter-leukin-7 (IL-7).

The in vitro culture medium may comprise the components listed for WIT-L in Table I. In one embodiment, the medium comprises the components listed in Table I, each present at the concentration listed; in other embodiments, the medium comprises the components listed in Table I, with at least one of the components present at a concentration that is about 5%, 10%, 20%, 50%, 100% higher or lower than what is listed. In certain embodiments, the medium further comprises one or more antibiotics, such as penicillin and/or streptomycin. In certain embodiments, the medium is prepared as a 1× solution, or a concentrated solution of about 2×, 5×, or 10×. In certain embodiments, at least some components of the medium is a concentrated at about 2×, 5×, 10×, 100×, or 1000×. In certain embodiments, at least some or all components of the medium are in liquid or aqueous form (e.g., F12 and M199 media). In certain embodiments, at least some components of the medium is in solid, powder, or frozen form (e.g., labile protein growth factors and steroid hormones).

EGF in any of the aforementioned in vitro cell culture media may be at a concentration from 1 ng/ml, from 5 ng/ml, from 10 ng/ml, up to 500 ng/ml, 2500 ng/ml, or any range therebetween (e.g., from 1 ng/ml to 2500 ng/ml).

Hydrocortisone in any of the aforementioned in vitro cell culture media may be at a concentration from 0.01 ng/ml, from 0.05 ng/ml, from 0.1 ng/ml, up to 5 ng/ml, up to 25 ng/ml, or any range therebetween (e.g., from 0.01 ng/ml to 5 ng/ml). Inclusion of hydrocortisone may be optional.

Insulin in any of the aforementioned in vitro cell culture media may be at a concentration from 0.2 µg/ml, from 1 µg/ml, from 2 µg/ml, up to 100 µg/ml, up to 500 µg/ml, or any range therebetween (e.g., from 0.2 µg/ml to 500 µg/ml).

SCF in any of the aforementioned in vitro cell culture media may be at a concentration from 1 ng/ml, from 5 ng/ml, from 10 ng/ml, up to 500 ng/ml, up to 2500 ng/ml, or any range therebetween (e.g., from 1 ng/ml to 2500 ng/ml).

IGF-1 in any of the aforementioned in vitro cell culture media may be at a concentration from 0.2 ng/ml, from 1 ng/ml, from 2 ng/ml, up to 100 ng/ml, up to 500 ng/ml, or any range therebetween (e.g., from 0.2 ng/ml to 500 ng/ml).

IL-2 in any of the aforementioned in vitro cell culture media may be at a concentration from 0.2 ng/ml, from 1 ng/ml, from 2 ng/ml, up to 100 ng/ml, up to 500 ng/ml, or any range therebetween (e.g., from 0.2 ng/ml to 500 ng/ml).

IL-7 in any of the aforementioned in vitro cell culture media may be at a concentration from 0.2 ng/ml, from 1 ng/ml, from 2 ng/ml, up to 100 ng/ml, up to 500 ng/ml, or any range therebetween (e.g., from 0.2 ng/ml to 500 ng/ml).

"Chemically defined" means the components of the in vitro culture medium are known or can be defined. In general, the inclusion of a tissue extract or blood product (e.g., thymus extract or serum) is not desirable because the amounts and the identities of each active substance therein is highly variable. Therefore, the aforementioned in vitro cell culture media may exclude a source of growth factors and hormones such as serum. Thus, the in vitro culture medium may be essentially serum free, contain less than 0.01% (vol/vol), contain less than 0.1% (vol/vol), contain less than 1% (vol/vol), or contain less than 10% (vol/vol) of serum.

The aforementioned in vitro cell culture media may also exclude one or more of FMS-like tyrosine kinase 3 ligand (Flt3L), macrophage colony stimulating factor (M-CSF), erythropoietin (Epo), granulocyte colony stimulating factor (G-CFS), interleukin-3 (IL-3), interleukin-6 (IL-6), or any combination thereof. In certain embodiments, agents that induce increased intracellular cAMP levels or directly increase intracellular cAMP levels are deliberately excluded from the medium. For example, an agent that induces increased intracellular cAMP levels may be an inhibitor of cAMP phosphodiesterase, a β-adrenergic receptor agonist, dibutyryl cAMP, isobutylmethylxanthine, theophylline, isoproterenol, cholera toxin, and forskolin. Thus, one or more of them may be excluded from the medium.

The in vitro cell culture medium may be used at least to maintain or to propagate a cancer cell, including a leukemia or lymphoma (e.g., T-ALL). The cell may be a primary cancer cell, especially of a lymphocyte lineage, obtained from a human patient. The patient may be a human child (younger than 18 years old), younger adult (from 18 years old to 30 years old), adult (from 30 years old to 60 years old), or older adult (over 60 years old). Such culturing may be used in a process for screening, isolating, cloning, identifying, analyzing, or any combination thereof one or more cancer cell(s). For example, cancer stem cells may be isolated, cancer cells expressing markers may be identified, and primary cells may be analyzed for one or more mutation(s) in specific gene sequences (e.g., NOTCH1 gene, PTEN gene, or FBXW7 gene) by sequencing or chromo-some rearrangement such as one or more of t(12;21) for a TEL-AML1 fusion, t(1;19)(q23;p13) for an E2A-PBX fusion, t(9;22)(q34;q11) for a BCR-ABL fusion, t(4;11)(q21;q23) for an MLL-AF4 fusion, t(8;14)(q24;q32) for an IGH-MYC fusion, and t(11;14)(p13;q11) for a TCR-RBTN2 fusion by cytogenetics, fluorescent in situ hybridization (FISH), or comparative genomic hybridization (CGH). Primary cancer cells may be maintained for at least ten days, at least 20 days, at least 30 days, or at least 60 days without senescence. Primary cancer cells may be propagated for at least ten population doublings, at least 20 population doublings, or at least 30 population doublings without senescence.

An in vitro cell culture medium comprised of at least inter-leukin-7 (IL-7) and a substrate at least partially covered by a ligand for Notch receptor may be used at least to maintain or to propagate a cancer cell, including a leukemia or lymphoma (e.g., T-ALL). The cell may be a primary cancer cell, especially of a lymphocyte lineage, obtained from a human patient. The patient may be a human child (younger than 18 years old), younger adult (from 18 years old to 30 years old), adult (from 30 years old to 60 years old), or older adult (over 60 years old). Such culturing may be used in a process for screening, isolating, cloning, identifying, analyzing, or any combination thereof one or more cancer cell(s). For example, cancer stem cells may be isolated, cancer cells expressing markers may be identified, and primary cells may be analyzed for one or more mutation(s) in specific gene sequences (e.g., NOTCH1, PTEN, or FBXW7 gene) by sequencing or chromosome rearrangement such as one or more of t(12;21) for a TEL-AML1 fusion, t(1;19)(q23;p13) for an E2A-PBX fusion, t(9;22)(q34;q11) for a BCR-ABL fusion, t(4;11)(q21;q23) for an MLL-AF4 fusion, t(8;14)(q24;q32) for an IGH-MYC fusion, and t(11;14)(p13;q11) for a TCR-RBTN2 fusion by cytogenetics, fluorescent in situ hybridization (FISH), or comparative genomic hybridization (CGH). Primary cancer cells may be maintained for at least ten days, at least 20 days, at least 30 days, or at least 60 days without senescence. Primary cancer cells may be propagated for at least ten population doublings, at least 20 population doublings, or at least 30 population doublings without senescence.

An in vitro culturing method of one or more human cancer cell(s), including a leukemia or lymphoma (e.g., T-ALL), may be comprised of incubating one or more cell(s) of a leukemia or lymphoma in an in vitro culture comprised of the in vitro cell culture medium. The in vitro culture may be further comprised of a substrate covered by a ligand for Notch receptor. The cell may be a primary cancer cell, especially of a lymphocyte lineage, obtained from a human patient. The patient may be a human child (younger than 18 years old), younger adult (from 18 years old to 30 years old), adult (from 30 years old to 60 years old), or older adult (over 60 years old). Such culturing may be used in a process for screening, isolating, cloning, identifying, analyzing, or any combination thereof one or more cancer cell(s). For example, cancer stem cells may be isolated, cancer cells expressing markers may be identified, and primary cells may be analyzed for one or more mutation(s) in specific gene sequences (e.g., NOTCH1 gene, PTEN gene, or FBXW7 gene) by sequencing or chromo-some rearrangement such as one or more of t(12;21) for a TEL-AML1 fusion, t(1;19)(q23;p13) for an E2A-PBX fusion, t(9;22)(q34;q11) for a BCR-ABL fusion, t(4;11)(q21;q23) for an MLL-AF4 fusion, t(8;14)(q24;q32) for an IGH-MYC fusion, and t(11;14)(p13;q11) for a TCR-RBTN2 fusion by cytogenetics, fluorescent in situ hybridization (FISH), or comparative genomic hybridization (CGH). Primary cancer cells may be maintained for at least ten days, at least 20 days, at least 30 days, or at least 60 days without senescence. Primary cancer cells may be propagated for at least ten population doublings, at least 20 population doublings, or at least 30 population doublings without senescence.

A process of screening for an agent that affects a human cancer cell, including a leukemia or lymphoma (e.g., T-ALL), cultured in accordance with the above. The process may be comprised of adding one or more candidate agents to an in vitro culture, which is comprised of human cancer cells and the aforementioned medium; measuring an activity or property of the human cancer cells in the presence of the one or more candidate agents; and selecting at least one agent, from among the candidate agents, that affects the human cancer cells by a change in the activity or property. For example, an activity or property of T-ALL that may be measured is cell viability, growth rate, cell cycle arrest and progression through the cell cycle, detection of cell-surface markers on T-ALL, and expression of genes specific for T-ALL. Cell proliferation rate, cell cycle profile, apoptosis, differentiation state, DNA damage, gene expression profile, half-maximal inhibitory concentration (IC50), metabolic rate, protein expression profile, and cell size and shape (cell morphometry) are among the measurements that can be made in a screen for anti-cancer agents. The selected agent may be formulated into a pharmaceutical composition or manufactured as a medicament.

A "leukemia" is a cancer of blood or bone marrow cells. Acute leukemia is characterized by a rapid increase in the numbers of immature blood cells. Chronic leukemia is characterized by relatively mature blood cells. Of particular interest here is lymphocytic leukemia. T cells may express terminal deoxynucleotidyl transferase (TdT), CD2, and CD7; B cells may express CD5, CD19, and surface immunoglobulin.

A "lymphoma" is a tumor of lymphoid cells (e.g., B or T cells) found in lymph nodes and extranodal sites. Of particular interest here is lymphocytic lymphoma. T cells may express terminal deoxynucleotidyl transferase (TdT), CD2, and CD7; B cells may express CD10 and surface immunoglobulin.

A "primary cell" is a cancer cell obtained from a human patient. A "primary cell line" is a cancer cell cultured in vitro. The cancer cell may be transported in or stored frozen under conditions that are traditionally used to freeze cell lines prior to in vitro culture. For example, cells can also be frozen in 10% (vol/vol) dimethyl sulfoxide (DMSO) in medium containing 20%-50% (vol/vol) serum in the vapor phase of a liquid nitrogen tank or in a special container that provides a slow 1° C. decrease in temperature during freezing. Alternatively, a commercially-available (e.g., Bambanker, Lymphotec, Wako Laboratory Chemicals) freeze down medium can be used according to the manufacturer's instructions.

"Maintenance" is the in vitro culture of human cancer cells of the lymphocyte lineage (e.g., a leukemia or a lymphoma), especially T-cell acute lymphoblastic leukemialymphoma (T-ALL), to maintain genotype and phenotype of the primary cancer cell(s).

"Propagation" is the in vitro culture of human cancer cells of the lymphocyte lineage (e.g., a leukemia or a lymphoma), especially T-cell acute lymphoblastic leukemialymphoma (T-ALL), for the primary cancer cell(s) to grow and divide.

"Senescence" of a primary culture of cells obtained from a human patient diagnosed with leukemia or lymphoma can be most simply deter-mined by cell morphology, β-galactosidase staining assay, growth arrest, and telomere shortening.

"Epidermal growth factor" (EGF) is a ligand for a tyrosine kinase transmembrane receptor (HER1). Binding of EGF to its receptor activates the RasMapk signaling modules. EGF may be provided as a recombinant protein (e.g., produced in bacteria) or purified from a natural source. The protein may have a human amino acid sequence.

"Hydrocortisone" is a steroid hormone that binds the glucocorticoid receptor (NR3C1). It might be replaced in the aforementioned in vitro culture media by an analog that specifically binds to the steroid hormone receptor (e.g., dexmethasone and prednisolone) or activates transcription by the same nuclear receptor. Hydrocortisone may be provided as a chemically synthesized steroid or purified from a natural source (e.g., adrenal gland).

"Insulin" is a ligand for a tyrosine kinase transmembrane receptor (CD220), consisting of two heterodimers of α and β subunits. It might be replaced in the aforementioned in vitro culture media by an analog that specifically binds to the IGF-1 receptor or activates the same tyrosine kinase. Insulin may be provided as a recombinant protein (e.g., produced in bacteria) or purified from a natural source. The protein may have a human or bovine amino acid sequence.

"Stem cell factor" (SCF) is a ligand for the Kit receptor (CD117). Binding of SCF to its receptor activates PI3-kinase, Src family kinases, and PLC gamma. It might be replaced in the aforementioned in vitro culture media by an analog that specifically binds to the SCF receptor or activates the same tyrosine kinase. But SCF is not replaced by Flt3L. SCF may be provided as a recombinant protein (e.g., produced in bacteria) or purified from a natural source. The protein may have a human amino acid sequence.

"Insulin-like growth factor-1" (IGF-1) is a ligand for a tyrosine kinase transmembrane receptor (CD221), consisting of two heterodimers of a and p subunits. It might be replaced in the aforementioned in vitro culture media by an analog that specifically binds to the IGF-1 receptor or activates the same tyrosine kinase. IGF-1 may be provided as a recombinant protein (e.g., produced in bacteria) or purified from a natural source. The protein may have a human amino acid sequence.

"Interleukin-2" (IL-2) is a ligand for the IL-2 receptor consisting of a specific alpha chain (CD25), a specific beta chain (CD122), and a common gamma chain (γc). Binding of IL-2 to its receptor activates the RasMapk, JakStat, and PI3-kinaseAkt signaling modules. It might be replaced in the aforementioned in vitro culture media by an analog that specifically binds to the IL-2 receptor or activates the same signaling pathways. IL-2 may be provided as a recombinant protein (e.g., produced in bacteria) or purified from a natural source. The protein may have a human amino acid sequence.

"Interleukin-7" (IL-7) is a ligand for the IL-7 receptor consisting of a specific alpha chain (IL7RA) and a common gamma chain (γc). Binding of IL-7 to its receptor mainly activates the JakStat signaling module. It might be replaced in the aforementioned in vitro culture media by an analog that specifically binds to the IL-7 receptor or activates the same signaling pathways. IL-7 may be provided as a recombinant protein (e.g., produced in bacteria) or purified from a natural source. The protein may have a human amino acid sequence.

"Notch ligand Delta-like-1" (DL1) is a ligand for Notch receptor. It might be replaced in the aforementioned in vitro culture media by an analog that specifically binds to Notch receptor (e.g., Jagged-1, Delta-like-2, Delta-like-3, or Delta-like-4) or activates the same signaling pathways. DL1 may be provided as a recombinant soluble protein (e.g., produced in mammalian cells) coated on a solid substrate on which cells are cultured or expressed as a transmembrane protein on the surface of mammalian cells. The protein may have a human amino acid sequence. When a feeder layer of cells is used in the in vitro culture, it is preferred that the cells are fixed or irradiated such that they cannot replicate and contaminate the primary cancer cell culture. T-ALL may be grown in suspension having only transient contact with the surface of the culture substrate.

"WIT-L" medium was made by mixing equal volumes of F12 (Sigma) and M199 media (JHR Biosciences) and supplementing with the following: 10 mM HEPES (pH 7.4), glutamine (2 mM), epidermal growth factor (0.5 ng/ml), hydrocortisone (0.5 ng/ml), insulin (10 µg/ml), stem cell factor (50 ng/ml), insulin-like growth factor-1 (10 ng/ml), interleukin-2 (10 ng/ml), interleukin-7 (10 ng/ml), transferrin (10 µg/ml), triiodothyronine (0.2 µg/ml), 0-phosphoryl ethanolamine (5 µg/ml), selenious acid (8 ng/ml), linoleic acid (5 µg/ml), and bovine serum albumin (1.25 mg/ml).

Screening of Candidate Agents

From a plurality of candidate agents (e.g., chemical compounds less than 600 molecular mass, nucleic acids, or proteins), one or more agents may be selected for treatment of cancer. The agent may be an enzyme substrate, receptor ligand, soluble receptor, antisense or siRNA nucleic acid, expression vector, antibody or fragment thereof, another specific binding molecule for a biomarker on the surface of or within the cancer cell, protein growth factor, or steroid hormone. For example, a signaling pathway required for maintenance, proliferation, or both of the cancer cell may be inhibited by the agent. It may reduce the cell's viability, slow the cell's growth rate, halt the cell's progression through the cell cycle, trigger the cell's apoptotic program, or differentiate the cell and cause it to stop dividing. The amount of the agent that is administered to a human patient in need of treatment, its formulation, and its timing and route of delivery is effective to treat the cancer. Determination of such amounts, formulations, and timing and route of drug delivery are within the skill in the art for each agent.

A screening process may comprise incubating a candidate compound with an in vitro cultured cancer cell, and then measuring an activity or property of the cancer cell. High-throughput screening assays are possible by using parallel processing and/or automated cell bioassay or imaging.

In an in vitro method of identifying a drug that reduces proliferation of human cancer cells, the method comprises: propagating one or more cancer cell(s) in an in vitro culture, in the presence of a candidate agent to be assessed for its ability to reduce proliferation of the cancer cell(s), under conditions appropriate for the agent to affect the cell(s); measuring the extent to which proliferation of the cancer cell(s) occurs in the presence of the candidate agent; and comparing the measurement with the extent to which proliferation of the cancer cell occurs under the same conditions but in the absence of the candidate agent, wherein if proliferation occurs to a lesser extent in the presence of the candidate agent than in its absence, the candidate agent is an agent that reduces proliferation of the cancer cell.

In an in vitro method of identifying a drug that inhibits or negatively affects at least one or more characteristic(s) of a cancer cell, the characteristic including: cell viability, growth rate, or progression through the cell cycle, the method comprises: propagating one or more cancer cell(s), in the presence of a candidate agent to be assessed for its ability to inhibit or negatively affect the one or more characteristic(s) of the cancer cell(s), under conditions appropriate for the agent to affect the cancer cell(s); measuring the extent to which the characteristic(s) is inhibited or negatively affected in the presence of the candidate agent; and comparing the measurement with the characteristic(s) of the cancer cell under the same conditions but in the absence of the candidate agent, wherein if the characteristic(s) is substantially inhibited or negatively affected in the presence of the candidate agent than in its absence, the candidate agent is an agent that inhibits or negatively affects one or more characteristic(s) of the cancer cell. In certain embodiments, the one or more characteristic(s) of the cancer cell is inhibited or negatively affected by at least about 20%, about 40%, about 60%, about 80%, about 90%, or about 95% in the presence of the agent than in its absence.

In an in vitro method of identifying a drug that enhances or positively affects one or more characteristic(s) of a cancer cell, the characteristic including: apoptosis, differentiation, sensitivity to chemotherapy or radiotherapy, or senescence, the method comprising: propagating one or more cancer cell(s), in the presence of a candidate drug to be assessed for its ability to enhance or positively affect the one or more characteristic(s) of the cancer cell(s), under conditions appropriate for the agent to affect the cancer cell(s); measuring the extent to which the characteristic(s) is enhanced or positively affected in the presence of the candidate drug; and comparing the measurement with the characteristic(s) of the cancer cell under the same conditions but in the absence of the candidate agent, wherein if the characteristic(s) is substantially enhanced or positively affected in the presence of the candidate agent than in its absence, the candidate agent is an agent that enhances or positively affects one or more the characteristic(s) of the cancer cell.

Formulation of Compositions

A selected agent or derivative thereof may be used to formulate a pharmaceutical composition or to manufacture a medicament with one or more of the utilities disclosed herein. They may be administered in vitro to cancer cells in culture, in vivo to cells in the patient's body, or ex vivo to cells outside of a patient that may then be returned to the body of the same patient.

An agent may be formulated into a pharmaceutical composition or manufactured into a medicament. The pharmaceutical composition or medicament may be further comprised of a carrier (e.g., water, dimethyl sulfoxide, or both), produced under aseptic conditions, assayed for the absence of endotoxin. The pharmaceutical composition or medicament may be further comprised of one or more excipient(s) useful for delivering the agent to its site of action or preventing the agent's degradation. The choice and addition of such carrier and excipient(s) to the pharmaceutical composition or medicament are within the level of skill in the art.

A pharmaceutical composition or medicament may be administered as a formulation which is adapted for direct application to the lymphatic system, or suitable for passage through at least the human patient's gut, blood, or lymph circulation. Alternatively, a pharmaceutical composition or medicament may be added to an in vitro culture containing cancer cells. The composition or medicament may be administered in a single dose or in multiple doses which are administered at different times.

A pharmaceutical composition may be administered by any known route. By way of example, the composition may be administered by a localized or systemic route (e.g., enteral and parenteral). In particular, achieving anti-cancer activity in or around an organ of the lymphatic system (e.g., bone marrow, thymus, lymph nodes, and lymphoid follicles in adenoids, tonsils, Peyer's patches, spleen, and skin) may be desired. This may involve use of local application, implantation near an organ, or infusion into the circulation.

The term "parenteral" includes subcutaneous, intradermal, intramuscular, intravenous, intraarterial, intrathecal, and other infusion techniques, without limitation.

Suitable choices in amounts and timing of doses, formulation, and routes of administration can be made with the goals of achieving anti-cancer activity in a human patient (i.e., efficacy), and avoiding undue toxicity or other harm thereto (i.e., safety). Therefore, "effective" refers to such choices that involve routine manipulation of conditions to achieve a desired anti-cancer effect.

A bolus of the formulation administered to a human patient once a day is a convenient dosing schedule. Alternatively, an effective dose may be administered every other day, once a week, or once a month. Dosage levels of active ingredients in a pharmaceutical composition can also be varied so as to achieve a transient or sustained concentration of the compound or derivative thereof in a subject and to result in the desired therapeutic response. But it is also within the skill of the art to start doses at levels lower than required to achieve the desired therapeutic effect and to gradually increase the dosage until the desired effect is achieved.

The amount of an agent administered is dependent upon factors such as, for example, bioactivity and bioavailability of the compound (e.g., half-life in the body, stability, and metabolism); chemical properties of the compound (e.g., molecular weight, hydrophobicity, and solubility); route and scheduling of administration; and the like. It will also be understood that the dose level to be achieved for a human patient may depend on a variety of factors, including age, gender, health, medical history, weight, combination with one or more other drugs, and severity of disease.

The term "treatment" refers to, inter alia, reducing or alleviating one or more symptoms of leukemia or lymphoma in a human patient. An in vitro result that could correlate with successful treatment of the patient is inducing at least apoptosis, cytotoxicity, or differentiation of one or more primary cancer cells. For a human patient, improvement in a symptom, its worsening, regression, or progression may be determined by any suitable objective or subjective measure. Treatment may also involve combination with existing modes of treatment (e.g., chemotherapy, radiation therapy, steroids, and bone marrow transplantation). Thus, combination treatment may be practiced.

Materials & Methods
Primary Human T-ALL Samples

Cryopreserved lymphoblast samples were provided by institutions in Canada (BC Children's Hospital), the United States of America (Karmanos Cancer Center and MD Anderson Cancer Center), and France (Hôpital Andre Trousseau). Primary diagnostic bone marrow aspirate samples were obtained at initial diagnosis or relapse with informed consent from patients or their legal guardians under approved institutional review board (IRB) protocols and following guidelines established in the Declaration of Helsinki.

Culture and Irradiation of MS5-DL1 Stromal Feeder Cells

MS5-DL1 stromal feeder cells were grown in alpha-MEM medium (Invitrogen) supplemented with 5% (vol/vol) fetal bovine serum (Invi-trogen, lot 306399), 2 mM Glutamax (Invitrogen), and 1× penicillin-streptomycin (StemCell Technologies). For studies using irradiated feeder cells, they were irradiated at a dose of 50 Gy. This dose was determined after testing a dose range from 20 Gy to 100 Gy. It damages the DNA of the feeder cells enough so that they cannot divide, but are still healthy enough to adhere to the plate and stay alive for around 7 days. Cells were plated into tissue culture treated plastic 12-well plates at a density of $8.5 \times 10^4$/well in 2 ml of medium. When 6-well plates were used, the cells were plated at $2.2 \times 10^5$/well in 3 ml of medium. Feeder cells were allowed to settle and adhere for a minimum of 4 hours before T-ALL were placed on top of them. When co-cultured with primary human T-ALL, the entire culture was grown in Pflumio or WIT-L medium. Primary T-ALL were passaged onto freshly irradiated feeders every 4-6 days.

Culture of Primary Human T-ALL

Primary human T-ALL were cultured in either alpha-MEM medium (Invitrogen) supplemented with 10% (vol/vol) fetal bovine serum (Invi-trogen, lot 306399), 10% (vol/vol) human AB serum (Mediatech), 50 ng/ml mouse SCF, 20 ng/ml mouse Flt3, 10 ng/ml mouse IL-7 (all from PeproTech), and 20 nM human Insulin (BCCA) or WIT-L medium supple-mented with 50 ng/ml mouse SCF, 10 ng/ml human IGF-1, 10 ng/ml human IL-2, and 10 ng/ml mouse IL-7 (all from PeproTech). When co-cultured with the MS5-DL1 stromal cells, either Pflumio or WIT-L medium was used. Cells were seeded into tissue culture treated plastic 12-well plates (Becton Dickinson) at $1.5 \times 10^6$ in 2 ml of medium. After 4-6 days, they were harvested, counted, and re-seeded at this density. This passage scheme continued until the cultures died. All studies were performed in triplicate.

IgDL1-Coated Tissue Culture Plates

A 12-well plate of tissue culture plastic was coated with immobilized DL1 ligand (Delta1$^{ext-IgG}$, kind gift of Dr. Irwin Bernstein, Fred Hutchinson Cancer Research Center) (Varnum-Finney et al., Blood 101:1784-1789, 2003). The IgDL1 was serially diluted in PBS and then 500 µl was plated at concentrations of 0.2 µg/ml, 1 µg/ml, or 2 µg/ml respectively. After 3-6 hours, the plates were washed with PBS to ensure that no non-adhered IgDL1 remained. Primary human T-ALL were then cultured on coated plates in one of the culture media previously described. All studies were performed in triplicate.

MS5-DL1 Conditioned Medium

MS5-DL1 cells were irradiated at 50 Gy and plated in alpha-MEM medium (Invitrogen) supplemented by 5% (vol/vol) fetal bovine serum (Invitrogen, lot 306399). After the feeder cells had adhered, the medium was removed and replaced with WIT-L basal medium supplemented with 50 ng/ml mouse SCF, 10 ng/ml human IGF-1, 10 ng/ml human IL-2, and 10 ng/ml mouse IL-7 (all from PeproTech). After 4 days, the medium was removed and filtered through a 0.45 µm sterile filter (Millipore catalog SLHV033RB). This conditioned media was used diluted at a 2:1 ratio with freshly made WIT-L medium supplemented with the four cytokines for all studies of conditioned medium.

Expansion of Primary Human T-ALL Samples in Immunodeficient Mice

NOD-scid/IL2rg$^{-/-}$ (NSG) mice were used as recipients for human T-ALL xenografts. Mice were housed in specific pathogen-free (SPF) animal facilities at the BC Cancer Agency Animal Resource Center and protocols were based on Canadian Council on Animal Care (CCAC) guidelines. The mice were sublethally irradiated at 200 rads, then injected intravenously in a lateral tail vein with $5-10 \times 10^6$ primary human T-ALL. Mice were monitored daily; those developing clinical signs of disease were sacrificed immediately and tissues harvested. Bone marrow from leukemic animals was harvested by flushing intramedullary cavities of femurs and tibias with 3% (vol/vol) fetal bovine serum in PBS. A cell suspension was filtered through 70 µm nylon mesh cell strainers (BD Falcon, catalog 352350) and red blood cells were lysed with ammonium chloride solution according to the manufacturer's protocol (Stem Cell Technologies). Cells were then resuspended in 3% (vol/vol) fetal bovine serum in PBS for subsequent processing. Splenocytes were harvested by mechanical disruption of explanted spleens in 3% (vol/vol) fetal bovine serum in PBS, followed by filtration through 70 μm nylon mesh and red blood cell lysis as described above. Cells were then resus-pended in fetal bovine serum (Invitrogen) supplemented with 10% DMSO and stored at −135° C. until used.

Resazurin Reduction Assay

Cell Titer Blue (Promega) was added to a co-culture, 5 μl/well for a 12-well plate and 1 μl/well for a 96-well plate, and allowed to incubate for 2-6 hours depending on the number and type of cells present in the well. Cultures were then analyzed using a Tecan GENios Flourometric plate reader. The plate reader was set to read from the bottom at 535 nm excitation and 590 nm emission wavelengths, at optimal gain with an integration time of 80 μs and a lag time of 0 μs. The plate was orbitally shaken in the machine for 5 sec prior to reading.

EXAMPLES

Cancer cells are obtained from a human patient: an adult who is 18 years or older, or a child who is younger than 18 years old. The cells may be primary cancer cells, especially those of a hematopoietic lineage. The primary tumor tissue can be directly cultured or initially stored (cooled at −1° C. per minute) in freezing medium containing 10% (vol/vol) dimethyl sulfoxide (DMSO) and 20%-50% (vol/vol) serum. Cells can be preserved in cryogenic vials in liquid nitrogen indefinitely, then thawed to start a new culture. The cells were cultured in 5% $CO_2$ and regular $O_2$ at 37° C. in tissue culture incubators. The cells were passaged by splitting at about 1:3 ratio once a week and plated into a new flask at greater than approximately $1 \times 10^4$ cells/cm$^2$. Single-cell suspensions of tumor tissue (1-5×10$^6$ cells per 100 μl volume) can be injected into immunodeficient mice. Tumors that grow in mice can be harvested from 4 to 24 weeks after implantation, which provides a much larger number of the tumor cells compared to the initial implantation. It has been shown in some cases, however, that the primary tumor cells and tumors harvested from the mice may have significant molecular differences due to clonal selection of the tumor cells while in mice. Thus, starting cultures directly from patient samples is preferred when possible.

"WIT-L" medium is made by mixing equal volumes of F12 (Sigma) and M199 media (JHR Biosciences) and supplementing with the following: 10 mM HEPES (pH 7.4), glutamine (2 mM), epidermal growth factor (0.5 ng/ml), hydrocortisone (0.5 ng/ml), insulin (10 μg/ml), stem cell factor (50 ng/ml), insulin-like growth factor-1 (10 ng/ml), interleukin-2 (10 ng/ml), interleukin-7 (10 ng/ml), transferrin (10 μg/ml), triiodothyronine (0.2 pg/ml), O-phosphoryl ethanolamine (5 μg/ml), selenious acid (8 ng/ml), linoleic acid (5 μg/ml), and bovine serum albumin (1.25 mg/ml).

The media disclosed herein can be made fresh every time from their individual components, which are commercially available from a variety of vendors, such as Sigma-Aldrich, Invitrogen, Lonza, Mediatech, Stemgent, etc. Alternatively, certain components of the media may be pre-made as high concentration stock solutions, which can be diluted to their final concentrations. A stock solution should be appropriately stored according to the characteristics of the components, including stability at the storage temperature (e.g., liquid nitrogen, −80° C., −20° C., 4° C., room temperature, or about 20-25° C., etc.), sensitiveness to light, natural half life in aqueous or organic solution, etc. Stock solutions should be remade periodically for freshness. The following describes examples of preparing several stock solutions. Other equivalent methods and similar, but not identical, concentrations of stock solutions may also be used.

Epidermal growth factor (EGF) from human or another mammal can be obtained from a commercial vender, such as Upstate Biotechnology. To prepare a stock solution (100 μg/ml): (1) retrieve an unopened vial of 100 μg human EGF from refrigerator; (2) make 0.1 mg/ml solution by adding 1.0 ml sterile distilled water to the vial (mix gently, but well; if necessary, vary the concentration according to the weight in the vial); (3) aliquot 0.26 ml portions into sterile ampoules; (4) optionally, confirm sterility by placing 3 μl from each ampoule in a 35-mm culture dish containing 1.5 ml medium and examining every day for contamination over 4 days; and (5) store frozen at −20° C. (discard stock after three months and make fresh).

Stocks for recombinant SCF, IGF-1, IL-2, and IL-7 (PeproTech or Calbiochem) were made either in PBS or in WIT-L culture medium at 100× concentration. Aliquots for single use were kept frozen at −80° C. until they were added to a 500 ml medium preparation.

Insulin can be obtained from a commercial vender, such as Sigma-Aldrich (catalog 1-5500). It may be purified from bovine or porcine pancreas, or produced recombinantly from bacteria expressing the human protein. To prepare a stock solution (1 mg/ml): (1) dissolve 1 g of insulin powder in 200 ml of 0.005 N HCl (1 ml of 1 N HCl in 199 ml of distilled water) by stirring on a magnetic stirrer; (2) when the solution is clear (if the solution does not clear, add a few drops of 1 N HCl but the total [HCl] should not exceed 0.005 N HCl), add 800 ml of distilled water to a final concentration of 1 mg/ml; (3) sterilize by filtering through 0.2 μm filter; (4) aliquot 2.8 ml or 26 ml into sterile polypropylene tubes; and (5) store frozen at −20° C.

Additionally, an in vitro cell culture medium may be prepared by adding other components to commercially available basal media. For example, Ham's F-12 Nutrient Mixture (1×) medium from GIBCO (catalog 11765-054) can be mixed with M-199 medium from Mediatech (catalog MT 10-060-CV) at 50:50 ratio. The mixture can then be supplemented with glutamine, transferrin, progesterone, testosterone, 17B-estradiol, O-phosphorylethanolamine, selenious acid, linoleic acid, bovine serum albumin (BSA), triiodothyronine (T3), HEPES, and other components to reach the desired final concentrations. Varying amounts, from none to the maximum concentration described above, of epidermal growth factor (EGF), hydrocortisone, insulin, stem cell factor (SCF), insulin-like growth factor-1 (IGF-1), interleukin-2 (IL-2), and interleukin-7 (IL-7) may be added to determine whether or not they are required. The medium may also contain antibiotics if desired, such as penicillin and/or streptomycin.

Pflumio medium can be used for in vitro culture of primary T-ALL using alpha-minimum essential medium (MEM) supplemented with 10% fetal calf serum, 10% human AB serum, human stem cell factor (50 ng/ml), FMS-like tyrosine kinase 3 ligand (20 ng/ml), insulin (20 nM), and IL-7 (10 ng/ml). To avoid using serum, which can vary in unpredictable ways from lot to lot, a serum-free, chemically defined WIT medium previously used for in vitro culture of mammary epithelium (Ince et al., Cancer Cell 12:160-170, 2007) was modified by excluding cholera toxin and including additional components to support the growth of T-ALL. Previously described versions of WIT media do not support growth of human T-ALL.

A head-to-head comparison was performed with human T-lymphoblasts directly cultured on an irradiated MS5-DL1 feeder layer in serum-containing Pflumio medium or serum-free WIT-L medium. In FIG. 1A, primary human T-ALL cells were passaged every 3-4 days on freshly irradiated feeder cells. In 4 of 4 cases studied, significantly greater (2-to 20-fold) cancer cell growth was observed in WIT-L medium than in Pflumio medium. The ability of DL1-coated plastic to substitute for MS5-DL1 feeder cells implies that no other factor that might be contacted on their cell surface or secreted into the medium is essential for culturing T-ALL.

Figure 1B:
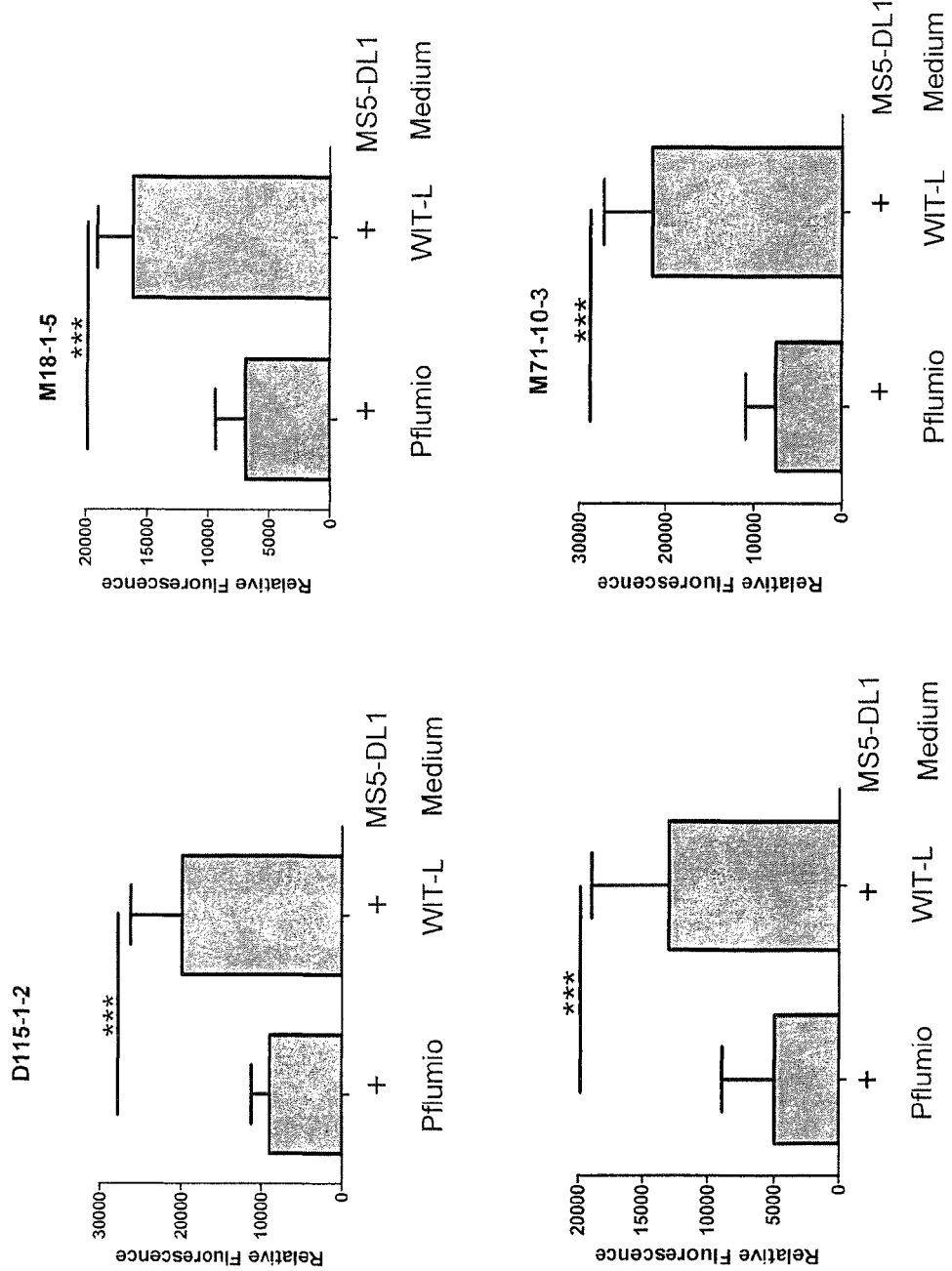

In FIG. 1B, human T-ALL cells were expanded in immunodeficient NOD scid gamma mice (i.e., NSG mice from Jackson Laboratory) before in vitro culture. In 4 of 4 cases studied, cancer cells grew more robustly in WIT-L medium than in Pflumio medium (2-to 20-fold more). Pflumio et al. reported that they could recover only up to 12 times more cells at day 30 compared with the input number of cells (Armstrong et al., Blood 113:1730-1740, 2009). Similar results were observed with Pflumio medium. In contrast, human T-ALL could be maintained in WIT-L medium for up to 60 days. Cancer cells in WIT-L medium were in vitro cultured up to 30 population doublings (i.e., $2^{30}$ or approximately $10^9$ fold expansion of T-ALL because every ten population doublings is roughly equal to 1000-fold expansion). The medium described by Pflumio et al. has been the most successful standard method of culturing human T-ALL until now. With Pflumio's method, it was only possible to recover 12-fold more human T-ALL compared to the input. Here, $10^9$ fold more cancer cells were recovered compared to the input using WIT-L medium.

Figure 2A:
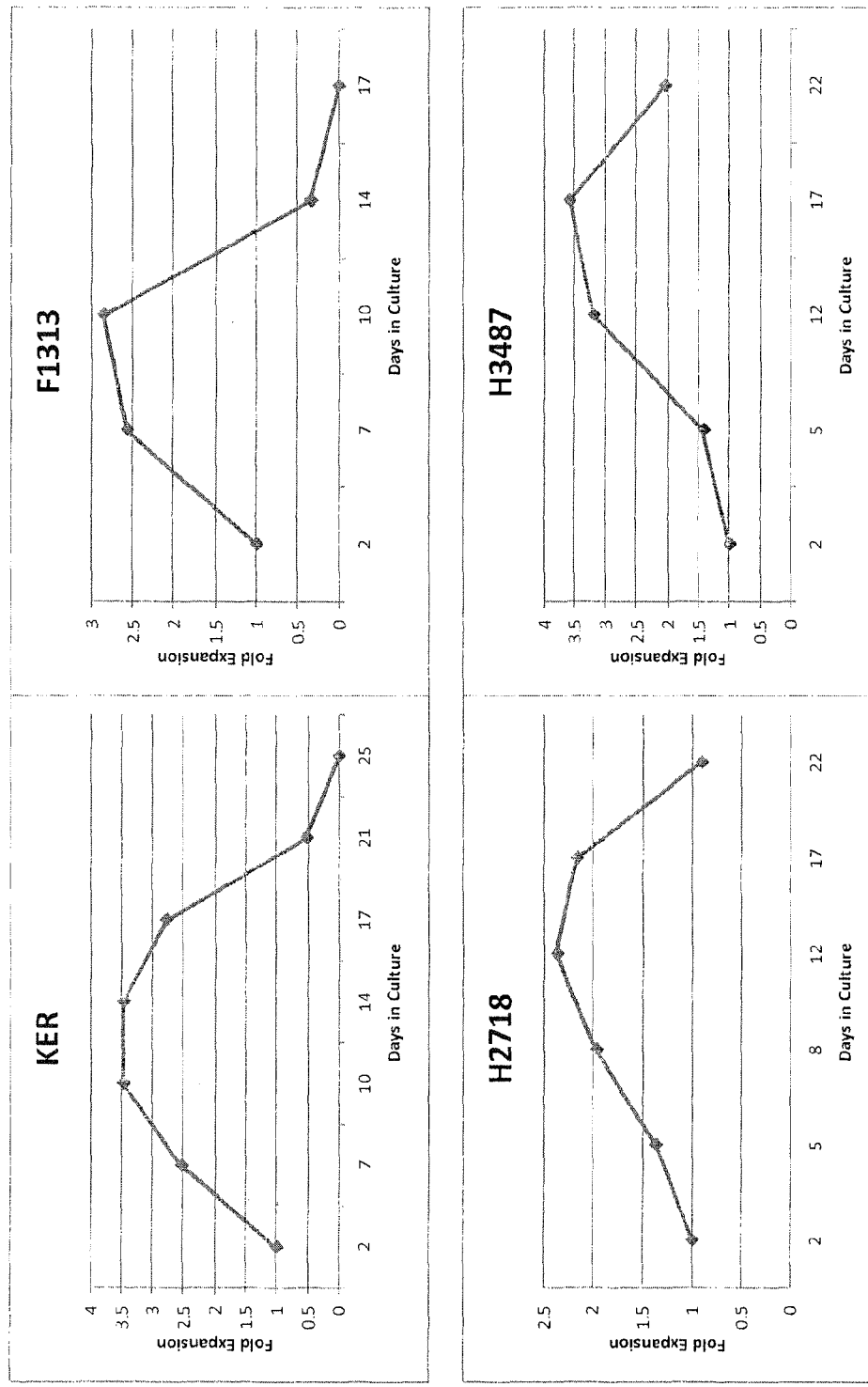
FIG. 2 shows that WIT-L medium supported maintenance and propagation of primary human T-ALL cultures in vitro for up to one month. Cells were expanded without undergoing crisis. The growth curves of cells from, (A) primary (n=4) and (B) xenograft-expanded T-ALL (n=4). Two $\times 10^6$ viable cells were seeded into each well of a 12-well dish and passaged every 4-6 days onto a fresh MS5-DL1 feeder layer. Viable cells were counted manually by trypan blue exclusion at each passage and reseeded at $2\times10^6$ cells in 0.5 ml to 1.0 ml medium per cm$^2$ (area of well bottom).
Figure 2B:
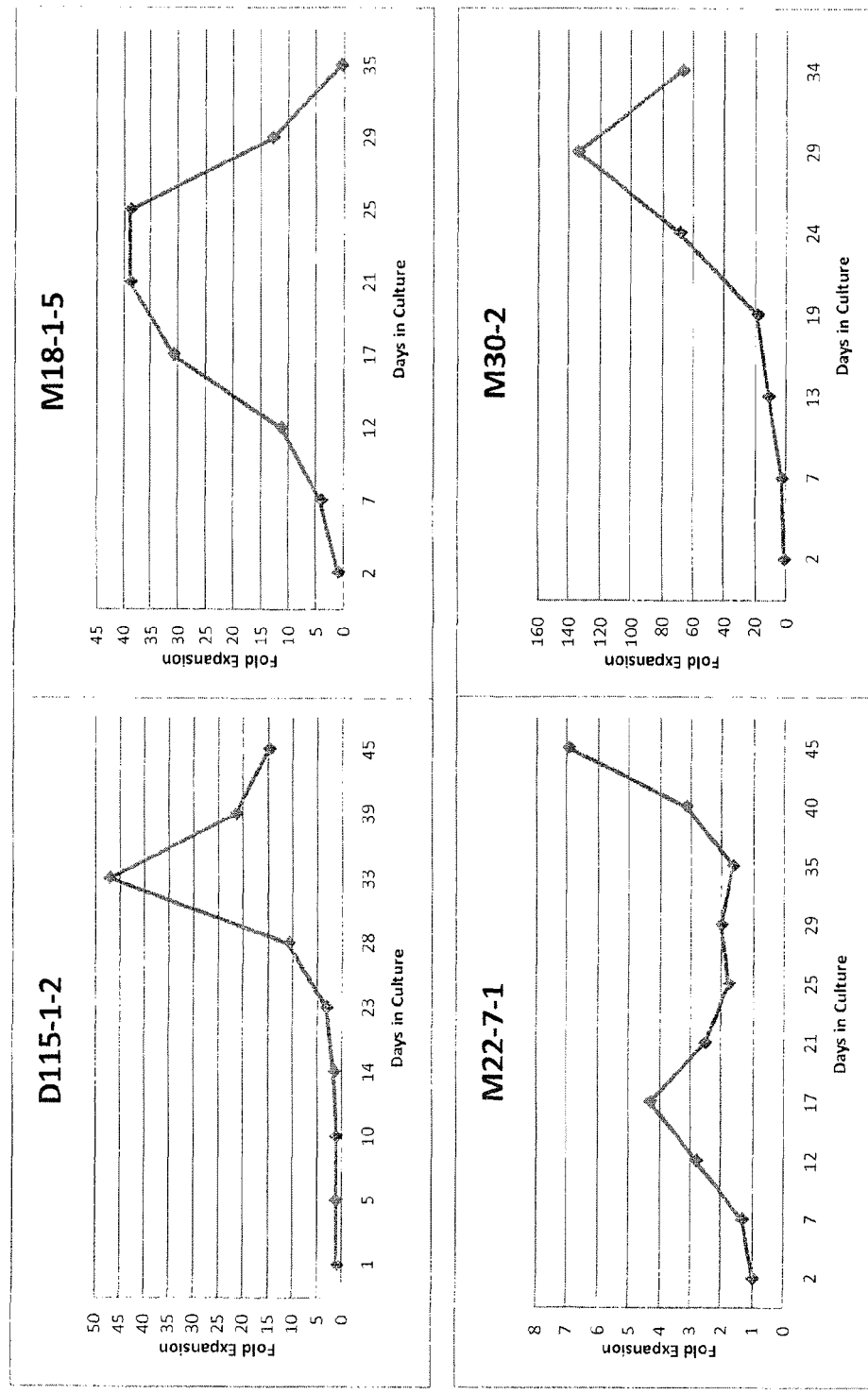

Subsequent studies were conducted with lymphoblasts obtained from human T-ALL derived directly from patient tumors. In 4 of 4 cases studied, significantly greater growth was observed in WIT-L medium than in Pflumio medium. In FIG. 2, there was a lag of 10 days or more before cells began to expand in Pflumio medium, suggesting that growth may stem from expansion of a minor clone following culture-induced crisis, while lymphoblasts in WIT-L medium began to expand within 1-2 days and increased by 3-4 fold in number within the first two weeks of culture, suggesting that most cells cultivated in WIT-L medium have proliferative potential.

Figure 3:
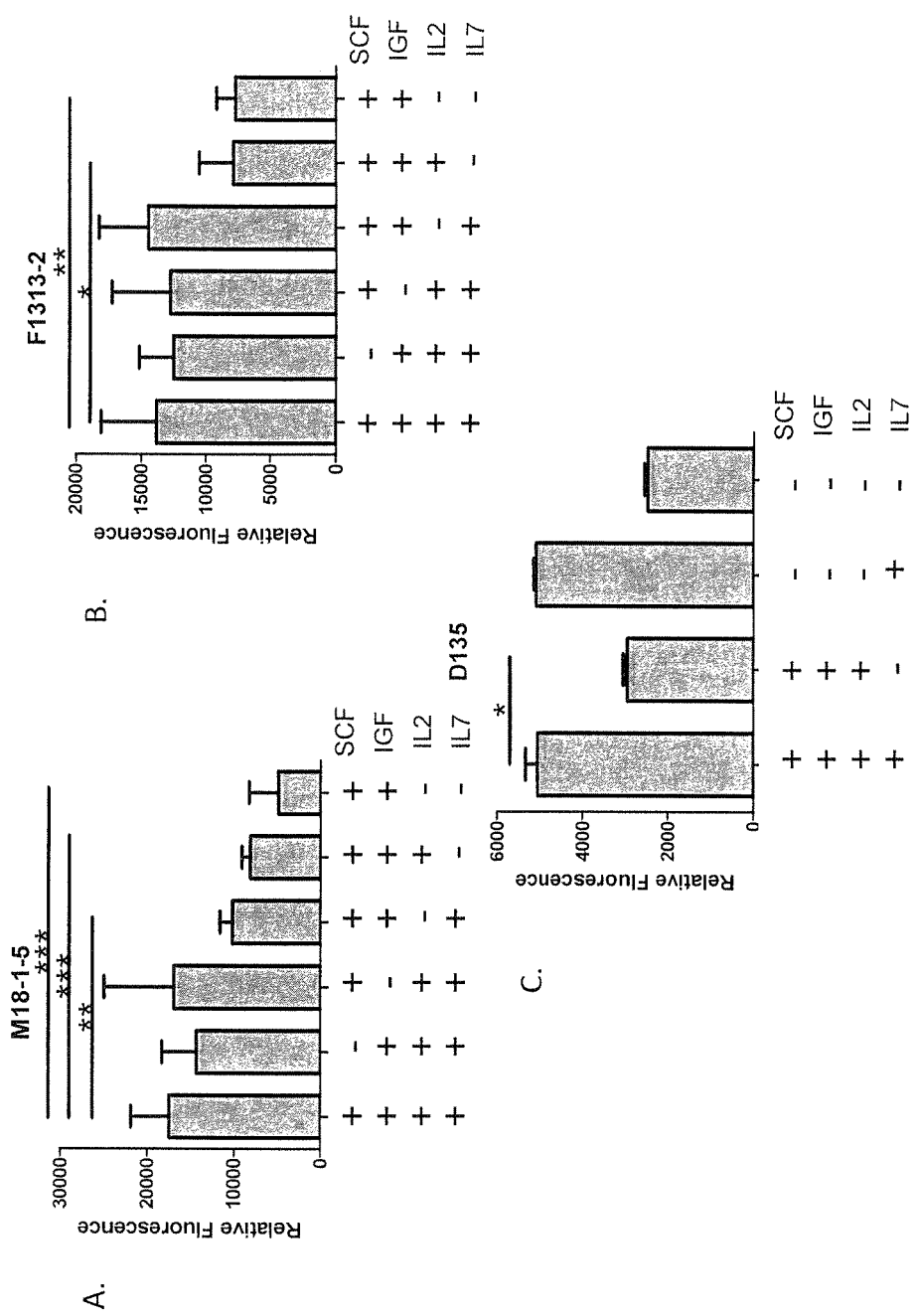
FIG. 3 shows interleukin-7 (IL-7) was necessary for in vitro growth of primary human T-ALL cultures. A resazurin-reduction cell growth assay was performed on (A-B) primary and (C) xenograft-expanded T-ALL. Cells were cultured and passaged as described in FIG. 1. Cytokines and growth factors were subtracted out of the complete media and cells were assayed for growth using a resazurin reduction assay. Data shown are a composite of passages 1 and 2. Significance: * $p<0.05$,  $p<0.01$, and * $p<0.001$.

Studies were also conducted with human T-ALL primary cells (FIGS. 3A-3B) and human T-ALL cells that were previously expanded in immunodeficient NSG mice (FIG. 3C). SCF, IGF-1, IL-2, and IL-7 were either added alone or in combination, then cancer cell growth was measured. Results in FIG. 3 indicate that better growth was achieved when all four cytokines are added to the in vitro culture medium. Supplemental IL-7 was the most important factor. IL-2 may improve growth of some tumors whereas IGF-1 may be dispensable as a supplement for in vitro culture media. CP-751,871, an IGF-1 receptor (IGF1R) blocking antibody, significantly impaired cell growth, suggesting that signaling through IGF1R does transduce important growth signals for lymphoblasts. This apparent paradox may be explained by the inclusion of high concentrations of insulin (20 mg/ml or 3.44 mM) in the basal medium. The Kd of insulin for IGF1R is 200-400 nM, making it possible that insulin in the basal medium stimulates IGF1R on lymphoblasts in the absence of IGF-1. Since CP-751,871 is specific for human IGF1R, indirect effects on the mouse MS5-DL1 feeders are unlikely.

Although it is possible not all human T-ALL will require the four cytokines equally. But the relative importance of each cytokine may change from case to case. In some tumors, elimination of one or two of these cytokines have small effects. But omission of one or more of these cytokines may have significant effects on other tumors. Optimizing the culture medium for each tumor is both time consuming and wastes precious samples. Thus, combination of all four cytokines as a uniform cocktail ensures reproducible results and is practical for most of the diverse human T-ALL.

Figure 4:
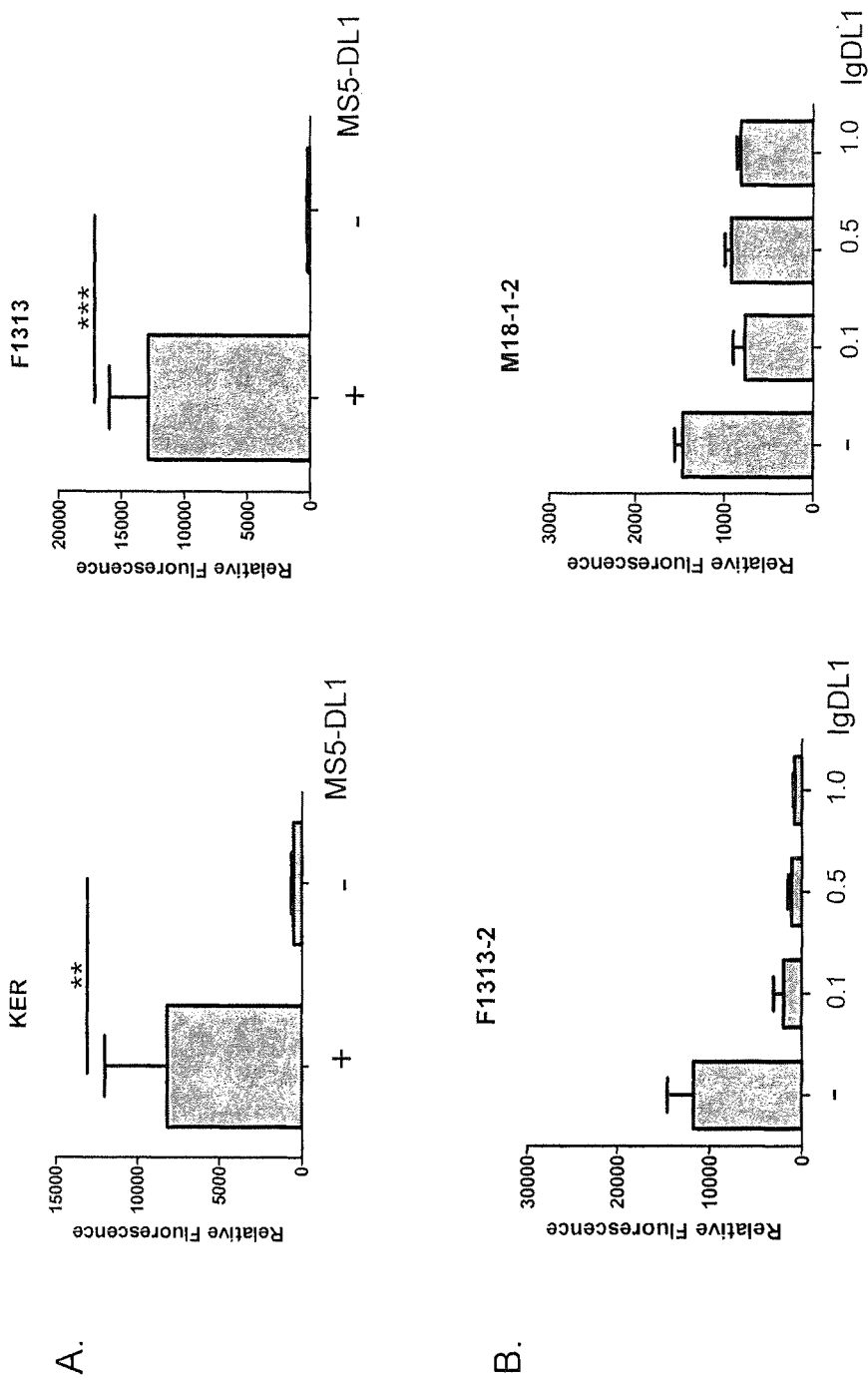
FIG. 4 shows interaction with a substrate covered by Notch ligand Delta-like-1 (DL1) protein was necessary for in vitro growth of primary human T-ALL cultures. A resazurin-reduction cell growth assay was performed on (A) primary and (B-C) xenograft-expanded T-ALL.

Human T-ALL cells were cultured on a feeder layer of mouse stromal cells that ectopically express Delta-like-1 (DL1) to activate Notch signaling and to promote blast cell growth. This demonstrates that human T-ALL grew significantly better on an MS5-DL1 feeder layer (FIG. 4A) and inhibition of Delta-like-1 with neutralizing antibodies inhibits cancer cell growth (FIG. 4B). This culture system suggests that DL1/Notch signaling is important for T-ALL proliferation. Alternative methods to activate DL1Notch signaling with small molecules and other biological reagents are possible. Thus, an alternative method of culture may use such a reagent to replace the feeder layer.

The culture medium described by Pflumio et al. has been the most successful standard method of culturing human T-ALL (Armstrong et al., Blood 113:1730-1740, 2009). Table I summarizes significant differences between the constituents of WIT-L and Pflumio media. The most significant difference is that all previously-reported media (including Pflumio) contain serum, which is an undefined substance containing thousands of unknown components. Thus, such media are difficult to improve, optimize, and maintain lot-to-lot consistency. In contrast, WIT-L medium is serum free and chemically defined; it does not contain any animal product, tissue extract, or other unknown components. In addition, IGF-1 and IL-2 are absent in Pflumio medium but present in WIT-L medium. In contrast, Flt3L is absent in WIT-L medium but present in Pflumio medium.

TABLE I

| Formulation of Media | | |
|---|---|---|
| | Pflumio | WIT-L |
| Basal media | aMEM | 50% F12 + 50% M199 Organic supplements |
| Human serum | 10% AB serum | — |
| Calf serum | 10% FCS | — |
| Insulin (human; MW 5808) | 20 nM (=116.16 ng/ml) | none added (10 ug/ml already in WITL) |
| SCF | 50 ng/ml | 50 ng/ml |
| Flt3L | 20 ng/ml | — |
| IGF-1 | — | 10 ng/ml |
| IL-2 | — | 10 ng/ml |
| IL-7 | 10 ng/ml | 10 ng/ml |

Table II describes clinical and genetic characteristics of patient T-ALL samples, including first diagnosis or relapse, and the presence or absence of Notch1, PTEN, and FBXW7 gene mutations.

TABLE II

Characteristics of Patient T-ALL Samples

| Sample ID | Diagnosis v Relapse | Age/Sex of patient | Notch1 HD mutation | Notch1 PEST mutation | PTEN mutation | FBXW7 mutation |
|---|---|---|---|---|---|---|
| KER | Diagnosis | <18 | WT | WT | WT | R479Q |
| M18 | Diagnosis | 6/M | WT | P2513L | WT | WT |
| M22 | Diagnosis | 7/M | WT | WT | 229 KGTGRQVHVL*/ 233 PGKTSSCTLSSLSRY LCVVISK* | WT |
| M30 | Diagnosis | 12/F | WT | Q2520* | WT | WT |
| M71 | Diagnosis | <18 | L1586P | WT | WT | WT |
| D115 | Diagnosis | <18 | WT | Q2459* | 245 YQFMFLVW* | WT |
| D135 | Diagnosis | <18 | WT | 2506 DLLPP* | 233 EEKTSSCTLSSLSRY LCVVISK* | WT |
| F1313 | Diagnosis | <18 | ND | ND | ND | ND |
| H2718 | Relapse | 19/M | ND | ND | 235 GKTSSCTLSSLSRYL CVVISK* | ND |
| H3487 | Relapse | 31/F | ND | ND | WT | ND |
| H2908 | Relapse | 28/M | ND | ND | WT | ND |
| H3255 | Relapse | 36/M | ND | ND | ND | ND |
| H3379 | Relapse | 28/M | ND | ND | ND | ND |

*Stop codon

Advantages of WIT-L medium are apparent in comparison to other culture media, especially Pflumio medium, in terms of the former's ability to support undifferentiated growth of isolated primary cells for substantial population doublings without going into senescence. T-ALL cells, which were obtained directly from patient biopsy material, showed growth in WIT-L medium in all cases superior to that observed in fetal bovine and human serum-containing medium (SCM). Further, when initially expanded as xenografts in immunodeficient mice then tested for growth in culture, T-ALL cells cultured in WIT-L grew significantly better than those cultured in SCM.

MS5 cells have been reported to secrete a variety of growth factors, including GM-CSF, IL-6, SCF, hepatocyte growth factor, and an IL-3-like activity as well as extracellular matrix proteins, including fibronectin, laminin, and type I collagen. When MS5-DL1 feeder cells were replaced with immobilized, recombinant DL1 ligand, T-ALL cells cultured in WIT-L medium or in MS5-DL1-conditioned WIT-L medium failed to grow, demonstrating that physical interaction with MS5 feeders and/or a secreted matrix protein provides critical signals for T-ALL cell growth.

Xenograft-expanded cells were also cultured in WIT-L medium and counted at passage (every 4-6 days) for up to six weeks. WIT-L cultures typically exhibited logarithmic growth, attaining maximal expansions of 40-to 100-fold when cultured at high density and 4000-to 10,000-fold when cultured at low density. Importantly, T-cell receptor gamma heteroduplex analysis confirmed expansion of the original clone throughout the culture period and flow cytometric analysis confirmed cultures to be composed entirely of immature T-lineage human cells. Of note, high-density cultures all began to regress after about 30 days, suggesting long-term renewing cells are not supported under these conditions. Low-density cultures did not show obvious regression; however, most were typically not carried beyond 30-50 days and thus are not particularly informative on this point. Finally, it is clear that while some patient samples expand very well in culture, others do not grow at all in either WIT-L or SCM media. Whether failure to grow in vitro is purely a technical problem (for example, pertaining to the quality of the sample) or reflects an inherent difference in growth requirements for a subset of T-ALLs remains to be determined. As an aside, although our data show that 9 of 9 samples cultured under both sets of conditions grew better in WIT-L than SCM, no samples were observed that grew well in WIT-L yet completely failed to expand in SCM.

This system has been used successfully in the laboratories of multiple different groups, suggesting that this completely defined system will prove to be easily adopted by other groups in the field. Up to 30% lentiviral transduction has been reported using Pflumio-cultured cells while up to 20% transduction has been achieved using WIT-L-cultured cells, suggesting that gene transfer and knock-down studies are possible using this system.

Patents, patent applications, and other publications cited herein are incorporated by reference in their entirety.

All and all modifications or substitutions that come within the meaning of the claims and the range of their legal equivalents are to be embraced within their scope. A claim using the transition "comprising" allows the inclusion of other elements to be within the scope of the claim; the invention is also described by such claims using the transitional phrase "consisting essentially of" (i.e., allowing the inclusion of other elements to be within the scope of the claim if they do not materially affect operation of the invention) and the transition "consisting" (i.e., allowing only the elements listed in the claim other than impurities or inconsequential activities which are ordinarily associated with the invention) instead of the "comprising" term. Any of the three transitions can be used to claim the invention.

An element described in this specification should not be construed as a limitation of the claimed invention unless it is explicitly recited in the claims. Thus, the claims are the basis for determining the scope of legal protection granted.

In contradistinction, the prior art is explicitly excluded from the invention to the extent of specific embodiments that would anticipate the claimed invention or destroy novelty. Moreover, no particular relationship between or among limitations of a claim is intended unless such relationship is explicitly recited in the claim (e.g., the arrangement of components in a product claim or order of steps in a method claim is not a limitation of the claim unless explicitly stated to be so). All possible combinations and permutations of the individual elements disclosed herein are considered to be aspects of the invention; similarly, generalizations of the invention's description are considered to be part of the invention.

From the foregoing, it would be apparent to a person of skill in this art that the invention can be embodied in other specific forms without departing from its spirit or essential characteristics. The described embodiments should be considered only as illustrative, not restrictive, because the scope of the legal protection provided for the invention will be indicated by the appended claims rather than by this specification.

What is claimed is:

1. An in vitro cell culture medium comprising
   (i) optionally epidermal growth factor (EGF),
   (ii) optionally hydrocortisone,
   (iii) optionally insulin,
   (iv) stem cell factor (SCF),
   (v) insulin-like growth factor- 1 (IGF-1),
   (vi) interleukin-2 (IL-2), and
   (vii) interleukin-7 (IL-7).

2. The medium of claim 1 further comprising one or more components selected from the group consisting of: precursors of lipid synthesis, precursors of protein synthesis, precursors of carbohydrate synthesis, precursors of energy metabolism, precursors in a catabolic or anabolic metabolic pathway, antioxidants, precursors of nucleotide synthesis in a salvage pathway, carrier proteins, surfactants, salts, buffers, and combinations thereof.

3. The medium of claim 1, wherein the EGF is present at a concentration from 5 ng/ml to 500 ng/ml.

4. The medium of claim 1, wherein the hydrocortisone is present at a concentration from 0.05 ng/ml to 5 ng/ml.

5. The medium of claim 1, wherein the insulin is present at a concentration from 1 pg/ml to 100 pg/ml.

6. The medium of claim 5, wherein the medium is essentially serum free.

7. The medium of claim 1, wherein the SCF is present at a concentration from 5 ng/ml to 500 ng/ml.

8. The medium of claim 1, wherein the IGF-1 is present at a concentration from 1 ng/ml to 100 ng/ml.

9. The medium of claim 1, wherein the IL-2 is present at a concentration from 1 ng/ml to 100 ng/ml.

10. The medium of claim 1, wherein the IL-7 is present at a concentration from 1 ng/ml to 100 ng/ml.

11. The medium of claim 1, wherein the medium contains less than 10% (vol/vol) of serum.

12. The medium of claim 1, wherein the medium is not comprised of FMS-like tyrosine kinase 3 ligand (Flt3L).

13. The medium of claim 1, wherein the medium is not comprised of erythropoietin (Epo).

14. The medium of claim 1, wherein the medium is not comprised of interleukin-3 (IL-3).

15. The medium of claim 1, which is capable of maintaining in vitro primary T-cell acute lymphoblastic leukemia/lymphoma cultured for at least ten days.

16. The medium of claim 1, which is capable of propagating in vitro primary T-cell acute lymphoblastic leukemia/lymphoma cultured for at least ten population doublings.

17. An in vitro cell culture medium according to claim 1, comprising: vitamin A, vitamin B1, vitamin B2, vitamin B3, vitamin B5, vitamin B6, vitamin B7, vitamin B9, vitamin B12, vitamin C, vitamin D, and vitamin E; zinc, magnesium, iron, copper, and selenium; transferrin and albumin; cholesterol, linoleic acid, and lipoic acid; triiodothyronine (T3); glucose; glutathione; adenosine triphosphate; phosphoethanolamine; and one or more precursor bases of a nucleotide salvage pathway selected from the group consisting of hypoxanthine, xanthine, adenine, guanine, and thymidine.

18. The in vitro cell culture medium of claim 17, further comprising one or more of epidermal growth factor (EGF); hydrocortisone; and insulin.

19. A method for in vitro culturing one or more cell(s) selected from the group consisting of human leukemias, human lymphomas, other human lymphoblasts, and precursors thereof, the method comprising: incubating the cell(s) in an in vitro culture comprised of the medium of claim 1.

20. The method according to claim 19, wherein the in vitro culture is further comprised of a substrate covered by a ligand for Notch receptor.

21. A method for in vitro culturing of one or more cell(s) selected from the group consisting of human leukemias, human lymphomas, other human lymphoblasts, and precursors thereof; the method comprising:
   (a) providing a (i) medium according to claim 1 containing at least interleukin-7 (IL-7) and (ii) a substrate covered by a ligand for Notch receptor, and
   (b) incubating the one or more cell(s) in an in vitro culture comprised of the medium and the substrate;
   wherein the cell(s) are bathed in the medium and contacted with a surface of the substrate.

22. The method according to claim 21, wherein the substrate is at least a feeder layer of cells expressing the ligand on their surface or a culture vessel having the ligand coated on its surface.

23. The medium of claim 1, wherein the medium contains less than 1% (vol/vol) of serum.

24. The medium of claim 1, wherein the medium contains less than 0.1% (vol/vol) of serum.

25. The medium of claim 1, wherein the medium contains less than 0.01% (vol/vol) of serum.

26. The medium of claim 1, wherein the medium is essentially serum free.

27. The medium of claim 1, wherein the medium is not comprised of interleukin-6 (IL-6).

28. The medium of claim 1, wherein the medium comprises neither interleukin-3 (IL-3) nor interleukin-6 (IL-6).

29. The medium of claim 1, wherein the medium is not comprised of macrophage colony stimulating factor (M-CSF).

30. The medium of claim 1, wherein the medium comprises neither Flt3L nor M-CSF.

31. The medium of claim 1, wherein the medium is not comprised of granulocyte colony stimulating factor (G-CSF).

32. The medium of claim 1, wherein the medium comprises neither Epo nor G-CSF.

33. The medium of claim 1, which is capable of maintaining in vitro primary T-cell acute lymphoblastic leukemia/lymphoma cultured for at least 20 days.

34. The medium of claim 1, which is capable of maintaining in vitro primary T-cell acute lymphoblastic leukemia/lymphoma cultured for at least 30 days.

35. The medium of claim 1, which is capable of maintaining in vitro primary T-cell acute lymphoblastic leukemia/lymphoma cultured for at least 60 days.

36. The medium of claim 1, which is capable of propagating in vitro primary T-cell acute lymphoblastic leukemia/lymphoma cultured for at least 20 population doublings.

37. The medium of claim 1, which is capable of propagating in vitro primary T-cell acute lymphoblastic leukemia/lymphoma cultured for at least 30 population doublings.

* * * * *

UNITED STATES PATENT AND TRADEMARK OFFICE
CERTIFICATE OF CORRECTION

PATENT NO. : 9,683,217 B2  Page 1 of 1
APPLICATION NO. : 14/394346
DATED : June 20, 2017
INVENTOR(S) : Tan Ince et al.

It is certified that error appears in the above-identified patent and that said Letters Patent is hereby corrected as shown below:

On the Title Page

In the left column between the "(65) Prior Publication Data" and (51) Int. Cl." sections, please insert:
-- Related U.S. Application Data
(60) Provisional application No. 61/623,539 filed on April 12, 2012 --

Signed and Sealed this
Seventh Day of November, 2017

Joseph Matal
*Performing the Functions and Duties of the*
*Under Secretary of Commerce for Intellectual Property and*
*Director of the United States Patent and Trademark Office*